US011872255B2

United States Patent
Balani et al.

(10) Patent No.: US 11,872,255 B2
(45) Date of Patent: *Jan. 16, 2024

(54) METHODS AND COMPOSITIONS OF PREVENTING AND TREATING DENTAL CARIES

(71) Applicant: Forsyth Dental Infirmary for Children, Cambridge, MA (US)

(72) Inventors: Pooja Balani, Melrose, MA (US); Felicitas Bidlack, Somerville, MA (US); Xuesong He, Cypress, CA (US); Megan Pugach-Gordon, Medford, MA (US); Wenyuan Shi, Winchester, MA (US); Jacqueline Starr, Lexington, MA (US); Daniel Ferrer, Boston, MA (US)

(73) Assignee: Forsyth Dental Infirmary for Children, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/575,160

(22) Filed: Jan. 13, 2022

(65) Prior Publication Data

US 2022/0241355 A1  Aug. 4, 2022

Related U.S. Application Data

(63) Continuation of application No. 17/119,933, filed on Dec. 11, 2020, now Pat. No. 11,246,895, which is a continuation of application No. PCT/US2020/063343, filed on Dec. 4, 2020.

(60) Provisional application No. 62/944,717, filed on Dec. 6, 2019.

(51) Int. Cl.
 *A61K 35/00* (2006.01)
 *A61K 35/747* (2015.01)
 *A61K 6/00* (2020.01)

(52) U.S. Cl.
 CPC .............. *A61K 35/747* (2013.01); *A61K 6/00* (2013.01)

(58) Field of Classification Search
 CPC .................................................... A61K 35/747
 See application file for complete search history.

(56) References Cited

U.S. PATENT DOCUMENTS

| 4,133,875 A | 1/1979 | Hillman |
| 11,246,895 B2 | 2/2022 | Balani et al. |
| 2018/0333440 A1 | 11/2018 | Finlay et al. |
| 2021/0169954 A1 | 6/2021 | Balani et al. |

FOREIGN PATENT DOCUMENTS

| JP | 2015/157768 A | 9/2015 |
| WO | WO-2021/113658 A1 | 6/2021 |

OTHER PUBLICATIONS

International Search Report and Written Opinion for International Application No. PCT/US2020/063343 dated Feb. 25, 2021.
Tsuzukibashi et al., "Isolation of identification methods of *Rothia* species in oral cavities," J Microbiol Methods, 134: 21-26 (2017).

*Primary Examiner* — Benjamin J Packard
(74) *Attorney, Agent, or Firm* — Foley Hoag LLP; Hathaway P. Russell

(57) ABSTRACT

Provided herein are methods and compositions related to bacteria of genus *Rothia* useful as therapeutic agents for dental caries.

13 Claims, 11 Drawing Sheets

- Spot 20 uL of OD 0.5 *S. mutans* or *Rothia* cells on BHI Agar plates with phenol red
- Grow overnight in $CO_2$ chamber
- Measure pH of each spot using a flat bottom pH probe.

Strep. infantis, Strep. sanguinis SK36, Strep. sobrinus, Lactobacillus fermentum

METHODS AND COMPOSITIONS OF PREVENTING AND TREATING DENTAL CARIES

This application is a continuation application of U.S. patent application Ser. No. 17/119,933, filed Dec. 11, 2020, which is a continuation application of International Patent Application No. PCT/US20/63343, filed Dec. 4, 2020, which claims the benefit of U.S. Provisional Application No. 62/944717, filed Dec. 6, 2019, the contents of each of which are incorporated by reference herein in its entirety.

STATEMENT OF RIGHTS

This invention was made with government support under grant numbers NIH-1-R01-DE020102 awarded by The National Institutes of Health. The U.S. government has certain rights in the invention.

CROSS-REFERENCE TO RELATED APPLICATIONS

This application is a continuation application of PCT/US20/63343, filed Dec. 4, 2020, which claims the benefit of U.S. Provisional Application No. 62/944,717, filed Dec. 6, 2019, the contents of each of which are incorporated by reference herein in its entirety.

BACKGROUND

Dental caries or cavities, also known as tooth decay, is an infectious disease ubiquitous in civilized populations. Its treatment costs billions of dollars per year and entails considerable discomfort. Caries, the destruction of enamel, dentin, or cementum, has a multifactorial etiology which includes host susceptibility and diet containing fermentable carbohydrates. The principal cariogenic microorganisms include *Streptococcus mutans* (*S. mutans*), Lactobacilli, *Actinomyces viscosus* serovar II, *Actinomyces naeslundii* and "Intermediate" *Actinomyces*, other Streptococci and yeasts. These microorganisms produce acids such as acetic and lactic acids from the dietary carbohydrates, which causes destruction of the tooth. Probiotics against cariogenic microorganisms have been used for combating dental caries. However, there is still great need for probiotics that specifically target acid production of these microorganisms.

SUMMARY

In some aspects, provided herein are methods and compositions related to the prevention, treatment and/or reduction of severity of dental caries in a subject (e.g., a human) comprising administering a bacterial composition comprising a bacterium of species *Rothia denticariosa*, a bacterium of species *Rothia aeria*, a bacterium of species *Rothia mucilaginosa*, or a combination thereof. In some aspects, provided herein are methods and compositions related to the inhibition of acid production by a cardiogenic bacterium (e.g., a bacterium of species *Streptococcus mutans*) in a subject (e.g., a human) comprising administering to the subject a bacterial composition comprising a bacterium of genus *Rothia*.

In some aspects, provided herein are methods of preventing dental caries in a subject comprising administering to the subject a therapeutically effective amount of a bacterial composition comprising a bacterium of species *Rothia denticariosa*, a bacterium of species *Rothia aeria*, a bacterium of species *Rothia mucilaginosa*, or a combination thereof. In some embodiments, the bacterial composition prevents dental caries by inhibiting acid production by a cariogenic bacterium. In some embodiments, the bacterial composition does not inhibit growth of a cariogenic bacterium. The cariogenic bacterium may be, for example, a bacterium of species *Streptococcus mutans*, such as a bacterium of strain ATCC UA140 or ATCC UA159. The cariogenic bacterium may be, for example, a bacterium of genus *Streptococcus*, such as *Streptococcus infantis*, *Streptococcus sanguinis* SK36, or *Streptococcus sobrinus*. The cariogenic bacterium may also be, for example, a bacterium of genus *Lactobacillus*, such as *Lactobacillus fermentum* and *Lactobacillus salivarius*. In certain embodiments, the subject is at risk of developing dental caries.

In some aspects, provided herein are methods of treating or reducing severity of dental caries in a subject comprising administering to the subject a therapeutically effective amount of a bacterial composition comprising a bacterium of species *Rothia denticariosa*, a bacterium of species *Rothia aeria*, a bacterium of species *Rothia mucilaginosa*, or a combination thereof. In some embodiments, the bacterial composition treats or reduces severity of dental caries by inhibiting acid production by a cariogenic bacterium. In some embodiments, the bacterial composition does not inhibit growth of a cariogenic bacterium. In certain embodiments, the cariogenic bacterium is a bacterium of species *Streptococcus mutans*, such as a bacterium of strain ATCC UA140 or ATCC UA159. The cariogenic bacterium may be, for example, a bacterium of genus *Streptococcus*, such as *Streptococcus infantis*, *Streptococcus sanguinis* SK36, or *Streptococcus sobrinus*. In certain other embodiments, the cariogenic bacterium is a bacterium of genus *Lactobacillus*, such as *Lactobacillus fermentum* and *Lactobacillus salivarius*. In certain embodiments, the subject is at risk of developing dental caries.

In some embodiments, at least 50%, 60%, 70%, 80%, 85%, 90%, 90%, 91%, 92%, 93%, 94%, 95%, 96%, 97%, 98% or 99% of the bacteria in the bacterial compositions described herein are bacteria of species *Rothia denticariosa*, *Rothia aeria*, *Rothia mucilaginosa*, or a combination thereof. In certain embodiments, substantially all of the bacteria in the bacterial compositions described herein are bacteria of species *Rothia denticariosa*, *Rothia aeria*, *Rothia mucilaginosa*, or a combination thereof. In some embodiments, the bacterial compositions described herein comprise at least $1\times10^5$, $5\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$ or $1\times10^9$ colony forming units (CFUs) of bacteria of species *Rothia denticariosa*, *Rothia aeria*, *Rothia mucilaginosa*, or a combination thereof.

In some aspects, provided herein are methods of inhibiting acid production by a cariogenic bacterium in a subject comprising administering to the subject a bacterial composition comprising a bacterium of genus *Rothia*. In some embodiments, the bacterial composition comprises at least one bacterium selected from a bacterium of species *Rothia denticariosa*, a bacterium of *Rothia aeria*, and a bacterium of *Rothia mucilaginosa*. In some embodiments, the bacterial composition does not inhibit growth of a cariogenic bacterium. In certain embodiments, the cariogenic bacterium is a bacterium of species *Streptococcus mutans*, such as a bacterium of strain ATCC UA140 or ATCC UA159. The cariogenic bacterium may be, for example, a bacterium of species *Streptococcus infantis*, *Streptococcus sanguinis*

SK36, or *Streptococcus sobrinus*. In certain other embodiments, the cariogenic bacterium is a bacterium of genus *Lactobacillus*, such as *Lactobacillus fermentum* and *Lactobacillus salivarius*. In certain embodiments, the subject is at risk of developing dental caries. In certain other embodiments, the subject is afflicted with dental caries. In certain embodiments, the bacterial composition prevents dental caries in the subject. In certain other embodiments, the bacterial composition treats or reduces severity of dental caries in the subject.

In some embodiments, at least 50%, 60%, 70%, 80%, 85%, 90%, 90%, 91%, 92%, 93%, 94%, 95%, 96%, 97%, 98% or 99% of the bacteria in the bacterial compositions described herein are bacteria of genus *Rothia*. In certain embodiments, substantially all of the bacteria in the bacterial compositions described herein are bacteria of genus *Rothia*. In some embodiments, the bacterial compositions described herein comprise at least $1\times10^5$, $5\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$ or $1\times10^9$ colony forming units (CFUs) of bacteria of genus *Rothia*.

Numerous embodiments are further provided that may be applied to any aspect of the present disclosure and/or combined with any other embodiment described herein. For example, in some embodiments, the bacterial compositions described herein are administered orally. In some embodiments, the bacterial compositions described herein are administered in two or more (e.g., three or more, four or more, or five or more doses). In some embodiments, the administration to the subject of the two or more doses are separated by at least 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, or 21 days. The bacterial compositions described herein may comprise live bacteria, attenuated bacteria, or killed bacteria. In some embodiments, a second bacterium is administered as part of an ecological consortium.

In some embodiments, the methods described herein further comprise administering to the subject one or more other therapies that prevent, treat, and/or reduce severity of dental caries. In some embodiments, the other therapies comprise the administration of another therapeutic bacterium (e.g., a second bacterial composition that inhibits growth of a cariogenic bacterium). In certain embodiments, the cariogenic bacterium is a bacterium of species *Streptococcus mutans*, such as a bacterium of strain ATCC UA140 or ATCC UA159. The cariogenic bacterium may be, for example, a bacterium of genus *Streptococcus*, such as *Streptococcus infantis, Streptococcus sanguinis* SK36, or *Streptococcus sobrinus*. In certain other embodiments, the cariogenic bacterium is a bacterium of genus *Lactobacillus*, such as *Lactobacillus fermentum* and *Lactobacillus salivarius*.

In some embodiments, the methods described herein further comprise administering a prebiotic to the subject. The prebiotic may be, for example, a fructooligosaccharide, a galactooligosaccharide, a trans-galactooligosaccharide, a xylooligosaccharide, a chitooligosaccharide, a soy oligosaccharides, a gentiooligosaccharide, an isomaltooligosaccharide, a mannooligosaccharide, a maltooligosaccharide, a mannanoligosaccharide, lactulose, lactosucrose, palatinose, glycosyl sucrose, guar gum, gum Arabic, tagalose, amylose, amylopectin, pectin, xylan, or a cyclodextrin.

In some embodiments, the subject is a mammal. In some embodiments, the mammal is selected from the group consisting of a dog, a cat, a cow, a horse, a pig, a donkey, a goat, a camel, a mouse, a rat, a guinea pig, a sheep, a llama, a monkey, a gorilla, a chimpanzee or a human. In certain embodiment, the mammal is a human (e.g., a child).

DETAILED DESCRIPTION

General

Figure 1A:
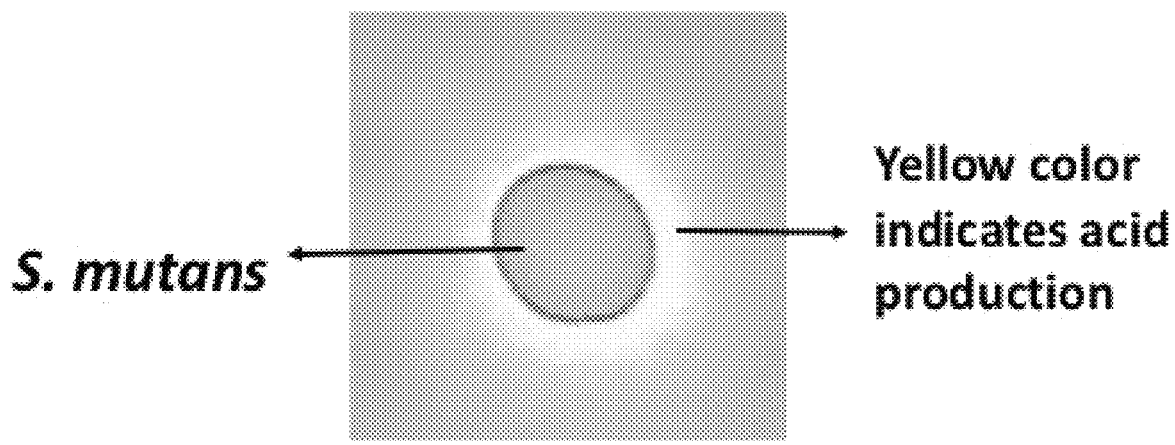
FIG. 1 contains two panels, FIGS. 1A and 1B, showing that bacteria of the genus *Rothia* inhibit acid production by *Streptococcus mutans*.

The present invention is based at least in part on the discovery that bacteria of the genus *Rothia* (e.g., bacteria from species *Rothia denticariosa*, bacteria from species *Rothia aeria*, and/or bacteria from species *Rothia mucilaginosa*), specifically inhibited acid production by a cariogenic bacterium (e.g., a bacterium of species *Streptococcus mutans* or a bacterium of genus *Lactobacillus*). Interestingly, these bacteria of the genus *Rothia*, did not inhibit the growth of the cariogenic bacterium. Acid production by a cariogenic bacterium, such as that of species *Streptococcus mutans*, is one of the major factors responsible for cavity production. The compostions comprising bacteria of genus *Rothia* can therefore be used to prevent, treat, and/or reduce severity of dental caries by targeted inhibition of acid production of cariogenic bacteria. The technical effects of the bacteria of the genus *Rothia* are different from many probiotics against cariogenic bacteria (e.g., *S. mutans*) available on the market which do not target the acid production.

Therefore, in some aspects, provided herein are methods and/or compositions of preventing, treating, and/or reducing severity of dental caries in a subject comprising administering to the subject a bacterial composition comprising a bacterium of genus *Rothia* (e.g., a bacterium from species *Rothia denticariosa*, a bacterium from species *Rothia aeria*, and/or a bacterium from species *Rothia mucilaginosa*). In some aspects, provided herein are methods and/or compositions of inhibiting acid production by a cariogenic bacterium (e.g., *S. mutans*) in a subject comprising administering to the subject a bacterial composition comprising a bacterium of genus *Rothia* (e.g., a bacterium from species *Rothia denticariosa*, a bacterium from species *Rothia aeria*, and/or a bacterium from species *Rothia mucilaginosa*).

Definitions

The singular forms "a," "an," and "the" include the plurals unless the context clearly dictates otherwise.

The terms "comprise" and "comprising" are used in the inclusive, open sense, meaning that additional elements may be included.

The term "effective amount" refers to that amount of a pharmaceutical composition which is sufficient to lead to a desired result. An effective amount of a pharmaceutical composition can be administered in one or more administrations.

The phrases "therapeutically-effective amount" and "effective amount" as used herein mean the amount of an agent which is effective for producing the desired therapeutic effect in at least a sub-population of cells in a subject at a reasonable benefit/risk ratio applicable to any medical treatment.

The term "cariogenic bacterium" refers to any oral bacterium that can cause dental caries. Cariogenic bacteria includes, but is not limited to, bacteria of genus *Mutans Streptococci* (e.g., *Streptococcus mutans* (*S. mutans*) or *Streptococcus sobrinus* (*S. sobrinus*)), or bacteria of genus *Lactobacilli*.

The term "prebiotic" refers to compounds in food that induce the growth or activity of beneficial microorganisms such as bacteria and fungi (e.g., a bacterium of genus *Rothia* used in the bacterial compostions described herein).

The term "probiotic" refers to microorganisms (e.g., the bacterial compostions described herein) that can provide health benefits when consumed. In some embodiments, the probiotics are live miroorganisms. In preferred embodiments, the probiotics are safe to consume, with minimal or no bacteria-host interactions or unwanted side effects.

The term "dental caries", also called "tooth decay" or "cavities", refers to a condition that is caused by breakdown of tooth enamel, dentin, or cementum. In some embodiments, this breakdown is the result of the bacteria on teeth that break down foods and produce acid that destroys tooth enamel.

"Adjuvant" or "adjuvant therapy" broadly refers to an agent that affects an immunological or physiological response in a patient or subject. For example, an adjuvant might increase the presence of an antigen over time or to an area of interest like a tumor, help absorb an antigen presenting cell antigen, activate macrophages and lymphocytes and support the production of cytokines. By changing an immune response, an adjuvant might permit a smaller dose of an immune interacting agent to increase the effectiveness or safety of a particular dose of the immune interacting agent. For example, an adjuvant might prevent T cell exhaustion and thus increase the effectiveness or safety of a particular immune interacting agent.

"Administration" broadly refers to a route of administration of a composition to a subject. Examples of routes of administration include oral administration, rectal administration, topical administration, inhalation (nasal) or injection. Administration by injection includes intravenous (IV), intramuscular (IM), intratumoral (IT) and subcutaneous (SC) administration. The pharmaceutical compositions described herein can be administered in any form by any effective route, including but not limited to intratumoral, oral, parenteral, enteral, intravenous, intraperitoneal, topical, transdermal (e.g., using any standard patch), intradermal, ophthalmic, (intra)nasally, local, non-oral, such as aerosol, inhalation, subcutaneous, intramuscular, buccal, sublingual, (trans)rectal, vaginal, intra-arterial, and intrathecal, transmucosal (e.g., sublingual, lingual, (trans)buccal, (trans)urethral, vaginal (e.g., trans- and perivaginally), intravesical, intrapulmonary, intraduodenal, intragastrical, and intrabronchial. In preferred embodiments, the pharmaceutical compositions described herein are administered orally, rectally, intratumorally, topically, intravesically, by injection into or adjacent to a draining lymph node, intravenously, by inhalation or aerosol, or subcutaneously.

The term "decrease" or "deplete" means a change, such that the difference is, depending on circumstances, at least 10%, 20%, 30%, 40%, 50%, 60%, 70%, 80%, 90%, 1/100, 1/1000, 1/10,000, 1/100,000, 1/1,000,000 or undetectable after treatment when compared to a pre-treatment state.

The term "ecological consortium" is a group of bacteria which trades metabolites and positively co-regulates one another, in contrast to two bacteria which induce host synergy through activating complementary host pathways for improved efficacy.

The term "gene" is used broadly to refer to any nucleic acid associated with a biological function. The term "gene" applies to a specific genomic sequence, as well as to a cDNA or an mRNA encoded by that genomic sequence.

"Identity" as between nucleic acid sequences of two nucleic acid molecules can be determined as a percentage of identity using known computer algorithms such as the "FASTA" program, using for example, the default parameters as in Pearson et al. (1988) Proc. Natl. Acad. Sci. USA 85:2444 (other programs include the GCG program package (Devereux, J., et al., Nucleic Acids Research 12(I):387 (1984)), BLASTP, BLASTN, FASTA Atschul, S. F., et al., J Molec Biol 215:403 (1990); Guide to Huge Computers, Mrtin J. Bishop, ed., Academic Press, San Diego, 1994, and Carillo et al. (1988) SIAM J Applied Math 48:1073). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.)).

The term "increase" means a change, such that the difference is, depending on circumstances, at least 10%, 20%, 30%, 40%, 50%, 60%, 70%, 80%, 90%, 2-fold, 4-fold, 10-fold, 100-fold, $10^{\wedge}3$ fold, $10^{\wedge}4$ fold, $10^{\wedge}5$ fold, $10^{\wedge}6$ fold, and/or $10^{\wedge}7$ fold greater after treatment when compared to a pre-treatment state. Properties that may be increased include immune cells, bacterial cells, stromal cells, myeloid derived suppressor cells, fibroblasts, metabolites, and cytokines.

The term "isolated" or "enriched" encompasses a microbe, bacteria or other entity or substance that has been (1) separated from at least some of the components with which it was associated when initially produced (whether in nature or in an experimental setting), and/or (2) produced, prepared, purified, and/or manufactured by the hand of man or human, or manufactured by humans. Isolated microbes may be separated from at least about 10%, about 20%, about 30%, about 40%, about 50%, about 60%, about 70%, about 80%, about 90%, or more of the other components with which they were initially associated. In some embodiments, isolated microbes are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. The terms "purify," "purifying" and "purified" refer to a microbe or other material that has been separated from at least some of the components with which it was associated either when initially produced or generated (e.g., whether in nature or in an experimental setting), or during any time after its initial production. A microbe or a microbial population may be considered purified if it is isolated at or after production, such as from a material or environment containing the microbe or microbial population, and a purified microbe or microbial population may contain other materials up to about 10%, about 20%, about 30%, about 40%, about 50%, about 60%, about 70%, about 80%, about 90%, or above about 90% and still be considered "isolated." In some embodiments, purified microbes or microbial population are more than about 80%, about 85%, about 90%, about 91%, about 92%, about 93%, about 94%, about 95%, about 96%, about 97%, about 98%, about 99%, or more than about 99% pure. In the instance of microbial compositions provided herein, the one or more microbial types present in the composition can be independently purified from one or more other microbes produced and/or present in the material or environment containing the microbial type. Microbial compositions and the microbial components thereof are generally purified from residual habitat products.

As used herein, a gene is "overexpressed" in a bacterium if it is expressed at a higher level in an engineered bacterium under at least some conditions than it is expressed by a wild-type bacterium of the same species under the same conditions. Similarly, a gene is "underexpressed" in a bacterium if it is expressed at a lower level in an engineered bacterium under at least some conditions than it is expressed by a wild-type bacterium of the same species under the same conditions.

The terms "polynucleotide" and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

"Operational taxonomic units" and "OTU(s)" refer to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S sequence or a portion of the 16S sequence. In other embodiments, the entire genomes of two entities are sequenced and compared. In another embodiment, select regions such as multilocus sequence tags (MLST), specific genes, or sets of genes may be genetically compared. For 16S, OTUs that share ≥97% average nucleotide identity across the entire 16S or some variable region of the 16S are considered the same OTU. See e.g. Claesson M J, Wang Q, O'Sullivan O, Greene-Diniz R, Cole J R, Ross R P, and O'Toole P W. 2010. Comparison of two next-generation sequencing technologies for resolving highly complex microbiota composition using tandem variable 16S rRNA gene regions. Nucleic Acids Res 38: e200. Konstantinidis K T, Ramette A, and Tiedje J M. 2006. The bacterial species definition in the genomic era. Philos Trans R Soc Lond B Biol Sci 361: 1929-1940. For complete genomes, MLSTs, specific genes, other than 16S, or sets of genes OTUs that share ≥95% average nucleotide identity are considered the same OTU. See e.g., Achtman M, and Wagner M. 2008. Microbial diversity and the genetic nature of microbial species. Nat. Rev. Microbiol. 6: 431-440. Konstantinidis K T, Ramette A, and Tiedje J M. 2006. The bacterial species definition in the genomic era. Philos Trans R Soc Lond B Biol Sci 361: 1929-1940. OTUs are frequently defined by comparing sequences between organisms. Generally, sequences with less than 95% sequence identity are not considered to form part of the same OTU. OTUs may also be characterized by any combination of nucleotide markers or genes, in particular highly conserved genes (e.g., "housekeeping" genes), or a combination thereof. Operational Taxonomic Units (OTUs) with taxonomic assignments made to, e.g., genus, species, and phylogenetic clade are provided herein.

The terms "subject" or "patient" refers to any animal. A subject or a patient described as "in need thereof" refers to one in need of a treatment for a disease. Mammals (i.e., mammalian animals) include humans, laboratory animals (e.g., primates, rats, mice), livestock (e.g., cows, sheep, goats, pigs), and household pets (e.g., dogs, cats, rodents). For example, the subject may be a non-human mammal including but not limited to of a dog, a cat, a cow, a horse, a pig, a donkey, a goat, a camel, a mouse, a rat, a guinea pig, a sheep, a llama, a monkey, a gorilla or a chimpanzee. The subject or patient may be healthy, may be at risk of developing dental caries, or may be suffering from dental caries at any developmental stage. In some embodiments, the subject has undergone a therapy that prevents, treats, and/or reduces severity of dental caries.

"Strain" refers to a member of a bacterial species with a genetic signature such that it may be differentiated from closely-related members of the same bacterial species. The genetic signature may be the absence of all or part of at least one gene, the absence of all or part of at least on regulatory region (e.g., a promoter, a terminator, a riboswitch, a ribosome binding site), the absence ("curing") of at least one native plasmid, the presence of at least one recombinant gene, the presence of at least one mutated gene, the presence of at least one foreign gene (a gene derived from another species), the presence at least one mutated regulatory region (e.g., a promoter, a terminator, a riboswitch, a ribosome binding site), the presence of at least one non-native plasmid, the presence of at least one antibiotic resistance cassette, or a combination thereof. Genetic signatures between different strains may be identified by PCR amplification optionally followed by DNA sequencing of the genomic region(s) of interest or of the whole genome. In the case in which one strain (compared with another of the same species) has gained or lost antibiotic resistance or gained or lost a biosynthetic capability (such as an auxotrophic strain), strains may be differentiated by selection or counter-selection using an antibiotic or nutrient/metabolite, respectively.

As used herein, the term "treating" a disease in a subject or "treating" a subject having or suspected of having a disease refers to subjecting the subject to a pharmaceutical treatment, e.g., the administration of one or more agents, such that at least one symptom of the disease is decreased or prevented from worsening. Thus, in one embodiment, "treating" refers inter alia to delaying progression, expediting remission, inducing remission, augmenting remission, speeding recovery, increasing efficacy of or decreasing resistance to alternative therapeutics, or a combination thereof.

As used herein, a therapeutic that "prevents" a condition (e.g., dental caries) refers to a composition that, when administered to a statistical sample prior to the onset of the disorder or condition, reduces the occurrence of the disorder or condition in the treated sample relative to an untreated control sample, or delays the onset or reduces the severity of one or more symptoms of the disorder or condition relative to the untreated control sample.

Bacteria

In certain aspects, provided herein are methods of using a bacterial composition comprising a bacterium of genus *Rothia*. The bacterium may be any *Rothia* species that is identified in oral cavity, or considered oral commensal bacterium. In some embodiments, the bacterium is of the species *Rothia denticariosa*, *Rothia aeria*, or *Rothia mucilaginosa*. In some embodiments, the bacterial composition comprises only one *Rothia* species (e.g., *Rothia denticariosa*, *Rothia aeria*, or *Rothia mucilaginosa*). In some other embodiments, the bacterial composition comprises more than one *Rothia* species, such as the combination of *Rothia denticariosa* and *Rothia aeria*, the combination of *Rothia denticariosa* and *Rothia mucilaginosa*, the combination of *Rothia aeria* and *Rothia mucilaginosa*, or the combination of *Rothia denticariosa*, *Rothia aeria*, and *Rothia mucilaginosa*.

In certain embodiments, at least 50%, 55%, 60%, 65%, 70%, 75%, 80%, 85%, 90%, 95% of the bacteria in the bacterial composition are of genus *Rothia*. In certain embodiments, substantially all of the bacteria in the bacterial composition are of genus *Rothia*.

*Rothia* strains may be selected for improved properties, including one or more of improved immunogenicity, improved selectivity for cariogenic microorganisms, decreased lymphadenitis, decreased virulence, decreased osteitis, increased resistance to reactive oxygen species (ROS), increased tolerance of low local pH or low local oxygen concentration (hypoxia), or other desired characteristics. In some embodiments, *Rothia* strains used herein are those regularly detected in oral cavity and/or are considered oral commensal bacterial strains.

In certain embodiments, the bacterial composition comprises at least $1\times10^3$ colony forming units (CFUs), $1\times10^4$ colony forming units (CFUs), $1\times10^5$ colony forming units (CFUs), $5\times10^5$ colony forming units (CFUs), $1\times10^6$ colony forming units (CFUs), $2\times10^6$ colony forming units (CFUs), $3\times10^6$ colony forming units (CFUs), $4\times10^6$ colony forming units (CFUs), $5\times10^6$ colony forming units (CFUs), $6\times10^6$ colony forming units (CFUs), $7\times10^6$ colony forming units (CFUs), $8\times10^6$ colony forming units (CFUs), $9\times10^6$ colony forming units (CFUs), $1\times10^7$ colony forming units (CFUs), $2\times10^7$ colony forming units (CFUs), $3\times10^7$ colony forming units (CFUs), $4\times10^7$ colony forming units (CFUs), $5\times10^7$ colony forming units (CFUs), $6\times10^7$ colony forming units (CFUs), $7\times10^7$ colony forming units (CFUs), $8\times10^7$ colony forming units (CFUs), $9\times10^7$ colony forming units (CFUs), $1\times10^8$ colony forming units (CFUs), $2\times10^8$ colony forming units (CFUs), $3\times10^8$ colony forming units (CFUs), $4\times10^8$ colony forming units (CFUs), $5\times10^8$ colony forming units (CFUs), $6\times10^8$ colony forming units (CFUs), $7\times10^8$ colony forming units (CFUs), $8\times10^8$ colony forming units (CFUs), $9\times10^8$ colony forming units (CFUs), $1\times10^9$ colony forming units (CFUs), $5\times10^9$ colony forming units (CFUs), $1\times10^{10}$ colony forming units (CFUs) of genus *Rothia*.

In certain embodiments, the bacterial composition comprises killed, live, or attenuated bacteria.

In some embodiments, the bacteria described herein are modified to improve colonization and/or engraftment in the mammalian mouth (e.g., modified metabolism, improved binding to the oral mucins, enhanced competition profile, increased motility, increased adhesion to dental plaque, or modified chemotaxis). In some embodiments, the bacteria described herein are modified to enhance their therapeutic effect on preventing, reducing or treating dental caries (e.g., either alone or in combination with another therapeutic agent). In some embodiments, the bacteria described herein are modified to improve bacterial manufacturing (e.g., higher oxygen tolerance, improved freeze-thaw tolerance, or shorter generation times).

Bacterial Compositions

In certain embodiments, the methods provided herein include the step of administering a bacterium and/or a combination of bacteria to a subject. In certain embodiments, the bacterium is administered to the subject in a bacterial formulation (i.e., a bacterial composition). In some embodiments, the bacterial formulation comprises a bacterium and/or a combination of bacteria described herein and a pharmaceutically acceptable carrier.

Methods for producing microbial compositions may include three main processing steps. The steps are: organism banking, organism production, and preservation. In certain embodiments, a sample that contains an abundance of *Rothia* may be cultured avoiding an isolation step.

For banking, the strains included in the microbial composition may be (1) isolated directly from a specimen or taken from a banked stock, (2) optionally cultured on a nutrient agar or broth that supports growth to generate viable biomass, and (3) the biomass optionally preserved in multiple aliquots in long-term storage.

In embodiments using a culturing step, the agar or broth may contain nutrients that provide essential elements and specific factors that enable growth. An example would be a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 mg/L hemin chloride, 2 mg/L calcium chloride, 1 mg/L menadione. Another example would be a medium composed of 10 g/L beef extract, 10 g/L peptone, 5 g/L sodium chloride, 5 g/L dextrose, 3 g/L yeast extract, 3 g/L sodium acetate, 1 g/L soluble starch, and 0.5 g/L L-cysteine HCl, at pH 6.8. A variety of microbiological media and variations are well known in the art (e.g., R. M. Atlas, *Handbook of Microbiological Media* (2010) CRC Press). Culture media can be added to the culture at the start, may be added during the culture, or may be intermittently/continuously flowed through the culture. The strains in the bacterial composition may be cultivated alone, as a subset of the microbial composition, or as an entire collection comprising the microbial composition. As an example, a first strain may be cultivated together with a second strain in a mixed continuous culture, at a dilution rate lower than the maximum growth rate of either cell to prevent the culture from washing out of the cultivation.

The inoculated culture is incubated under favorable conditions for a time sufficient to build biomass. For microbial compositions for human use this is often at 37° C. temperature, pH, and other parameter with values similar to the normal human niche. The environment may be actively controlled, passively controlled (e.g., via buffers), or allowed to drift. For example, for anaerobic bacterial compositions, an anoxic/reducing environment may be employed. This can be accomplished by addition of reducing agents such as cysteine to the broth, and/or stripping it of oxygen. As an example, a culture of a bacterial composition may be grown at 37° C., pH 7, in the medium above, pre-reduced with 1 g/L cysteine-HCl.

When the culture has generated sufficient biomass, it may be preserved for banking. The organisms may be placed into a chemical milieu that protects from freezing (adding 'cryoprotectants'), drying ('lyoprotectants'), and/or osmotic shock ('osmoprotectants'), dispensing into multiple (optionally identical) containers to create a uniform bank, and then treating the culture for preservation. Containers are generally impermeable and have closures that assure isolation from the environment. Cryopreservation treatment is accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term microbial composition storage stability at temperatures elevated above cryogenic conditions. If the microbial composition comprises, for example, spore forming species and results in the production of spores, the final composition may be purified by additional means such as density gradient centrifugation and preserved using the techniques described above. Microbial composition banking may be done by culturing and preserving the strains individually, or by mixing the strains together to create a combined bank. As an example of cryopreservation, a microbial composition culture may be harvested by centrifugation to pellet the cells from the culture medium, the supernatant decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Microbial production may be conducted using similar culture steps to banking, including medium composition and culture conditions described above. It may be conducted at larger scales of operation, especially for clinical development or commercial production. At larger scales, there may be several subcultivations of the microbial composition prior to the final cultivation. At the end of cultivation, the culture is harvested to enable further formulation into a dosage form for administration. This can involve concentration, removal of undesirable medium components, and/or introduction into a chemical milieu that preserves the microbial composition and renders it acceptable for administration via the chosen route. For example, a microbial composition may be cultivated to a concentration of $10^{10}$ CFU/mL, then concentrated 20-fold by tangential flow microfiltration; the spent medium may be exchanged by diafiltering with a preservative medium consisting of 2% gelatin, 100 mM trehalose, and 10 mM sodium phosphate buffer. The suspension can then be freeze-dried to a powder and titrated.

After drying, the powder may be blended to an appropriate potency, and mixed with other cultures and/or a filler such as microcrystalline cellulose for consistency and ease of handling, and the bacterial composition formulated as provided herein.

In certain aspects, provided are bacterial compositions for administration subjects. In some embodiments, the bacterial compositions are combined with additional active and/or inactive materials in order to produce a final product, which may be in single dosage unit or in a multi-dose format.

In some embodiments, the composition comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

In some embodiments, the composition comprises at least one lipid. As used herein, a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In some embodiments the composition comprises at least one modified lipid, for example a lipid that has been modified by cooking.

In some embodiments, the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In some embodiments, the composition comprises at least one supplemental vitamin. The at least one vitamin can be fat-soluble or water-soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

In some embodiments, the composition comprises an excipient. Non-limiting examples of suitable excipients include a buffering agent, a preservative, a stabilizer, a binder, a compaction agent, a lubricant, a dispersion enhancer, a disintegration agent, a flavoring agent, a sweetener, and a coloring agent.

In some embodiments, the excipient is a buffering agent. Non-limiting examples of suitable buffering agents include sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In some embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof.

In some embodiments, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments, the composition comprises a dispersion enhancer as an excipient. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments, the composition comprises a disintegrant as an excipient. In some embodiments the disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. In some embodiments the disintegrant is an effervescent disintegrant. Non-limiting examples of suitable effervescent disintegrants include sodium bicarbonate in combination with citric acid, and sodium bicarbonate in combination with tartaric acid.

In some embodiments, the composition is a food product (e.g., a food or beverage) such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Specific examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, and Chinese soups; soups; dairy products such as milk, dairy beverages, ice creams, cheeses, and yogurts; fermented products such as fermented soybean pastes, yogurts, fermented beverages, and pickles; bean products; various confectionery products, including biscuits, cookies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

In certain embodiments, the bacteria disclosed herein are administered in conjunction with a prebiotic to the subject. Prebiotics are carbohydrates which are generally indigestible by a host animal and are selectively fermented or metabolized by bacteria. Prebiotics may be short-chain carbohydrates (e.g., oligosaccharides) and/or simple sugars (e.g., mono- and di-saccharides) and/or mucins (heavily glycosylated proteins) that alter the composition or metabolism of a microbiome in the host. The short chain carbohydrates are also referred to as oligosaccharides, and usually contain from 2 or 3 and up to 8, 9, 10, 15 or more sugar moieties. When prebiotics are introduced to a host, the prebiotics affect the bacteria within the host and do not directly affect the host. In certain aspects, a prebiotic composition can selectively stimulate the growth and/or activity of one of a limited number of bacteria in a host. Prebiotics include oligosaccharides such as fructooligosaccharides (FOS) (including inulin), galactooligosaccharides (GOS), trans-galactooligosaccharides, xylooligosaccharides (XOS), chitooligosaccharides (COS), soy oligosaccharides (e.g., stachyose and raffinose) gentiooligosaccharides, isomaltooligosaccharides, mannooligosaccharides, maltooligosaccharides and mannanoligosaccharides. Oligosaccharides are not necessarily single components and can be mixtures containing oligosaccharides with different degrees of oligomerization, sometimes including the parent disaccharide and the monomeric sugars. Various types of oligosaccharides are found as natural components in many common foods, including fruits, vegetables, milk, and honey. Specific examples of oligosaccharides are lactulose, lactosucrose, palatinose, glycosyl sucrose, guar gum, gum Arabic, tagalose, amylose, amylopectin, pectin, xylan, and cyclodextrins. Prebiotics may also be purified or chemically or enzymatically synthesized.

Administration

In certain aspects, provided herein is a method of delivering a bacterial composition described herein to a subject. In some embodiments of the methods provided herein, the bacterial composition is administered in conjunction with the administration of a second therapeutic for preventing, treating, or reducing severity of dental caries. Such second therapeutic includes but is not limited to a probiotic, an antibiotic, a vaccine, and a chemotherapeutic agent. In certain embodiments, the second therapy is a second bacterial composition (e.g., a bacterial composition that reduces number of a cariogenic microorganism). In some embodiments, the first and the second bacterial compositions target the same cariogenic microorganism. In other embodiments, the first and the second bacterial compositions target different cariogenic microorganisms.

In some embodiments, the bacteria are co-formulated in a pharmaceutical composition with the second therapy. In some embodiments, the bacteria are co-administered with the second therapy. In some embodiments, the second therapy is administered to the subject before administration of the bacteria (e.g., about 1, 2, 3, 4, 5, 6, 7, 8, 9, 10, 15, 20, 25, 30, 35, 40, 45, 50 or 55 minutes before, about 1, 2, 3, 4, 5, 6, 7, 8, 9, 10, 11, 12, 13, 14, 15, 16, 17, 18, 19, 20, 21, 22 or 23 hours before, or about 1, 2, 3, 4, 5, 6, 7, 8, 9, 10, 11, 12, 13 or 14 days before). In some embodiments, the second therapy is administered to the subject after administration of the bacteria (e.g., about 1, 2, 3, 4, 5, 6, 7, 8, 9, 10, 15, 20, 25, 30, 35, 40, 45, 50 or 55 minutes after, about 1, 2, 3, 4, 5, 6, 7, 8, 9, 10, 11, 12, 13, 14, 15, 16, 17, 18, 19, 20, 21, 22 or 23 hours after, or about 1, 2, 3, 4, 5, 6, 7, 8, 9, 10, 11, 12, 13 or 14 days after). In some embodiments, the same mode of delivery is used to deliver both the bacteria and the second therapy. In some embodiments different modes of delivery are used to administer the bacteria and the second therapy. For example, in some embodiments, the bacteria are administered orally while the second therapy is administered via injection (e.g., an intravenous, intramuscular and/or intratumoral injection).

In certain embodiments, the pharmaceutical compositions, dosage forms, and kits described herein can be administered in conjunction with any other conventional therapy for managing dental caries, such as, for example, dietary and oral hygiene measures, removal of enamel and/or dentin exhibiting the signs of active caries, or protection of any newly exposed non-carious enamel and/or dentin with restorative material. These treatments may be applied as necessary and/or as indicated and may occur before, concurrent with or after administration of the pharmaceutical compositions, dosage forms, and kits described herein.

The dosage regimen can be any of a variety of methods and amounts, and can be determined by one skilled in the art according to known clinical factors. As is known in the medical arts, dosages for any one patient can depend on many factors, including the subject's species, size, body surface area, age, sex, immunocompetence, and general health, the particular microorganism to be administered, duration and route of administration, the kind and stage of the disease, for example, caries severity index (csi), and other compounds such as drugs being administered concurrently. In addition to the above factors, such levels can be affected by the infectivity of the microorganism, and the nature of the microorganism, as can be determined by one skilled in the art. In the present methods, appropriate minimum dosage levels of microorganisms can be levels sufficient for the microorganism to survive, grow and replicate in the mouth. The dose of the pharmaceutical compositions described herein may be appropriately set or adjusted in accordance with the dosage form, the route of administration, the degree or stage of a target disease, and the like.

In some embodiments, the dose administered to a subject is sufficient to prevent dental caries, delay its onset, or slow or stop its progression. One skilled in the art will recognize that dosage will depend upon a variety of factors including the strength of the particular compound employed, as well as the age, species, condition, and body weight of the subject. The size of the dose will also be determined by the route, timing, and frequency of administration as well as the existence, nature, and extent of any adverse side-effects that might accompany the administration of a particular compound and the desired physiological effect.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. An effective dosage and treatment protocol can be determined by routine and conventional means, starting e.g., with a low dose in laboratory animals and then increasing the dosage while monitoring the effects, and systematically varying the dosage regimen as well. Animal studies are commonly used to determine the maximal tolerable dose ("MTD") of bioactive agent per kilogram weight. Those skilled in the art regularly extrapolate doses for efficacy, while avoiding toxicity, in other species, including humans.

In accordance with the above, in therapeutic applications, the dosages of the active agents used in accordance with the invention vary depending on the active agent, the age, weight, and clinical condition of the recipient patient, and the experience and judgment of the clinician or practitioner administering the therapy, among other factors affecting the selected dosage. In some embodiments, the dose should be sufficient to result in slowing the tooth destruction, and preferably restoring the tooth, and most preferably causing complete restoration of the tooth. In some embodiments, the dose should be sufficient to result in reducing the acid production by a cariogenic microorganism (e.g., *S. mutans*), and most preferably causing a complete stop of the acid production by a cariogenic microorganism (e.g., *S. mutans*).

Separate administrations can include any number of two or more administrations (e.g., doses), including two, three, four, five or six administrations. One skilled in the art can readily determine the number of administrations to perform, or the desirability of performing one or more additional administrations, according to methods known in the art for monitoring therapeutic methods and other monitoring methods provided herein. In some embodiments, the doses may be separated by at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days or 1, 2, 3, or 4 weeks. Accordingly, the methods provided herein include methods of providing to the subject one or more administrations of a bacterium, where the number of administrations can be determined by monitoring the subject, and, based on the results of the monitoring, determining whether or not to provide one or more additional administrations. Deciding on whether or not to provide one or more additional administrations can be based on a variety of monitoring results, including, but not limited to, indication of acid production, appearance of new dental cavities, the subject's anti-bacterium antibody titer, the overall health of the subject and/or the weight of the subject.

The time period between administrations can be any of a variety of time periods. The time period between administrations can be a function of any of a variety of factors, including monitoring steps, as described in relation to the number of administrations, the time period for a subject to mount an immune response and/or the time period for a subject to clear the bacteria from normal tissue. In one example, the time period can be a function of the time period for a subject to mount an immune response; for example, the time period can be more than the time period for a subject to mount an immune response, such as more than about one week, more than about ten days, more than about two weeks, or more than about a month; in another example, the time period can be less than the time period for a subject to mount an immune response, such as less than about one week, less than about ten days, less than about two weeks, or less than about a month. In another example, the time period can be a function of the time period for a subject to clear the bacteria from normal tissue; for example, the time period can be more than the time period for a subject to clear the bacteria from normal tissue, such as more than about a day, more than about two days, more than about three days, more than about five days, or more than about a week.

In some embodiments, the delivery of a second therapeutic that prevents, treats, and/or reduces severity of dental caries in combination with the bacterial composition described herein reduces the adverse effects and/or improves the efficacy of the second therapeutic.

The effective dose of a second therapeutic that prevents, treats, and/or reduces severity of dental caries is the amount of the therapeutic agent that is effective to achieve the desired therapeutic response for a particular patient, composition, and mode of administration, with the least toxicity to the patient. The effective dosage level can be identified using the methods described herein and will depend upon a variety of pharmacokinetic factors including the activity of the particular compositions administered, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. In general, an effective dose of a second therapeutic that prevents, treats, and/or reduces severity of dental caries will be the amount of the therapeutic agent which is the lowest dose effective to produce a therapeutic effect. Such an effective dose will generally depend upon the factors described above.

In some embodiments, the administration of the bacterial composition prevents, treats, and/or reduces severity of dental caries in the subject. In some embodiments, the bacterial composition inhibits acid production by a cariogenic microorganism (e.g., *S. mutans*) in the subject.

EXAMPLES

Example 1: Bacteria of the Genus *Rothia* Inhibit Acid Production by *Streptococcus mutans*

Figure 1B:
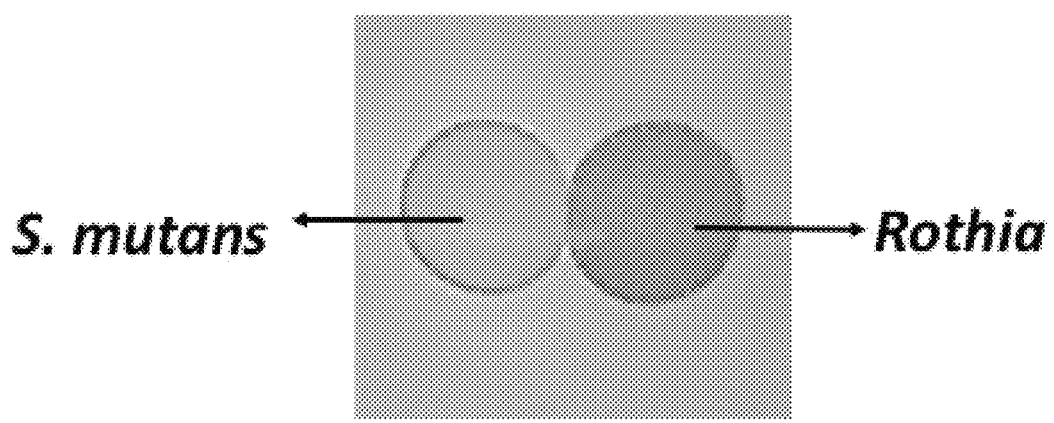

*S. mutans* is a major cariogenic pathogen, which causes its destruction of the tooth by production of high amounts of acid. A study was carried out to investigate the interaction between *S. mutans* and other commensal oral bacterial species. It was found that several oral *Rothia* species, including *R. denticariosa, R. mucilaginosa*, and *R. aeria*, inhibited the acid production by *S. mutans* UA140 or UA159 without significantly impact *S. mutans*' growth. Specifically, cultures of three strains of *Rothia* (*R. denticariosa* ATCC 17931, *R. mucilaginosa* ATCC 25296 and *R. aeria* F0183 which is from the Forsyth Institute strain collection), and two ATCC strains of *S. mutans* (*S. mutans* UA140 and *S. mutans* UA159) were cultured. A 10 µl drop (about 10^6 cells) of an overnight *Rothia* sp. culture was placed right next to a 10 µl drop (about 10^6 cells) of an overnight *S. mutans* culture, as shown in FIG. 1B, on a plate containing a pH indicator Phenol Red. This indicator turns from pink to yellow in the presence of acid. As a control, the 10 µl drop of *S. mutans* culture alone showed that acid production turned the color of agar from pink to yellow (FIG. 1A). Intriguingly, when *S. mutans* grew side-by-side with *Rothia* species, the color of the agar surrounding *S. mutans* no longer turned yellow, but remained pink. Meanwhile, the colony of *S. mutans* in the close vicinity of *Rothia* sp. grew normal compared to *S. mutans* growing by itself, with no obvious growth inhibition. These data suggested that *S. mutans*' acid production, but not growth was inhibited by the presence of the *Rothia* species (FIG. 1B).

Example 2: Additional Studies

Clinical isolates of *Rothia* sp. and *S. mutans* are isolated to perform additional studies. These studies include to test if clinical *Rothia* strains are capable of inhibiting acid production of the ATCC *S. mutans* strains when grown together in culture media and in mammalian cell cultures. It is also tested that whether clinical *Rothia* strains are capable of inhibiting acid production of the *S. mutans* strains isolated from the same plaque samples, when grown together in culture media as well as in the presence of mammalian cell. In addition, it is tested whether the *Rothia* strains as a mixed species culture (consisting of two or more strains), are able to inhibit acid production by *S. mutans* (ATCC and clinical strains), when grown together in culture media as well as in the presence of mammalian cell, or tooth surface. Moreover, whether *Rothia* species are able to inhibit tooth decay by *S. mutans*, by incubating samples of human teeth, including whole, partial, or a section of a tooth, in the presence of *Rothia* mixed with *S. mutans* is tested. Samples of human teeth include shed teeth, which are exfoliated primary teeth. It is also tested on permanent teeth and extracted teeth. Furthermore, it was tested whether *Rothia* species are able to inhibit the acid production of acidogenic bacterial species other than *S. mutans*, which either use a similar or different acid production pathway. Lastly, the detailed molecular mechanisms of *Rothia* sp.-mediated inhibition of *S. mutans* acid production was investigated.

Examples 3: Proximity Inhibition Setup

Figure 2A:
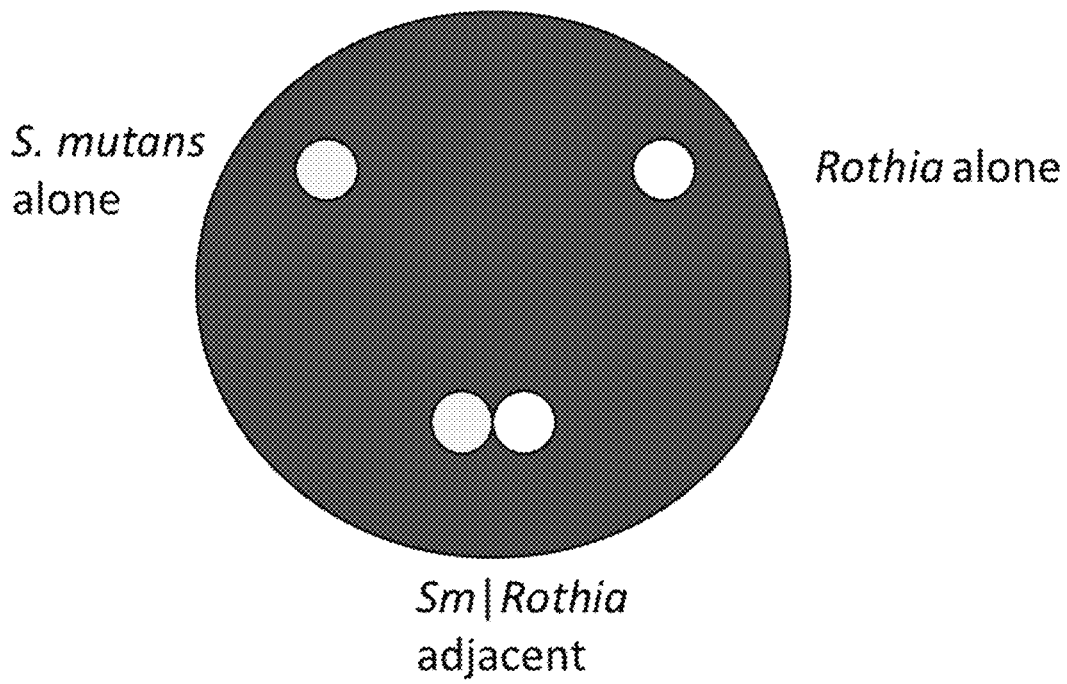
FIG. 2A shows a schematic diagram of the proximity inhibition setup.

Protocol: The proximity inhibition setup is shown in FIG. 2A. The cells of *Rothia* and *S. mutans* were grown overnight at 37° C. in shaking aerobic or aerobic +5% CO2 conditions, respectively. The cell cultures had their optical density measured and were diluted to OD600 0.5 in fresh BHI (Brain Heart Infusion media) liquid media. 20 µL of each culture were spotted onto a BHI agar (BHI media with 1.5% agar to solidify it) plate with the pH indicator Phenol red, alone as well as adjacent to each other, but not touching. Phenol red is a pH indicator that changes color based on the pH of the agar plate. The color is yellow at a low pH (<6) and red at higher pHs (>7) The phenol red serves as an immediate visual sign that there has been acid production. This assay is typically used for quantifying pH of bacterial colonies on agar plates.

Example 4: *Rothia* Significantly Inhibited Acid Production by Sm When Grown Adjacent to it Goal: Quantify the difference in local pH of a colony of *S. mutans* grown by itself and one grown adjacent to species of bacteria from the genus *Rothia*.

Figure 2B:
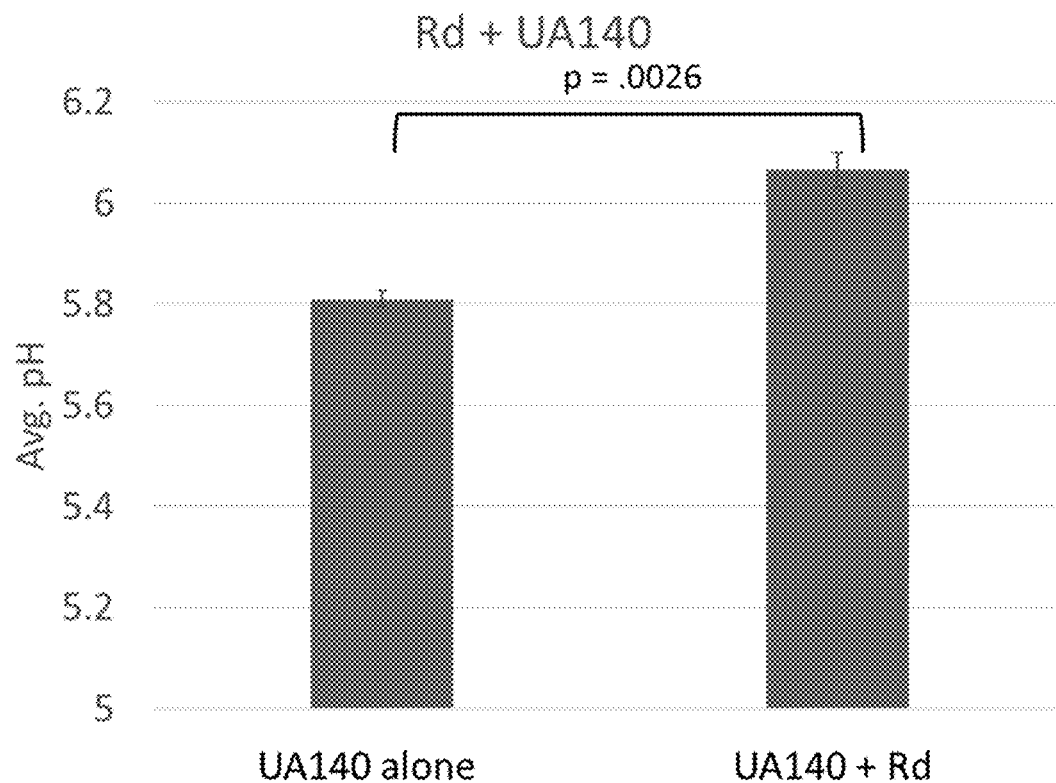
FIGS. 2B-2G show that *Rothia* significantly inhibited acid production by Sm when grown adjacent to it.
Figure 2C:
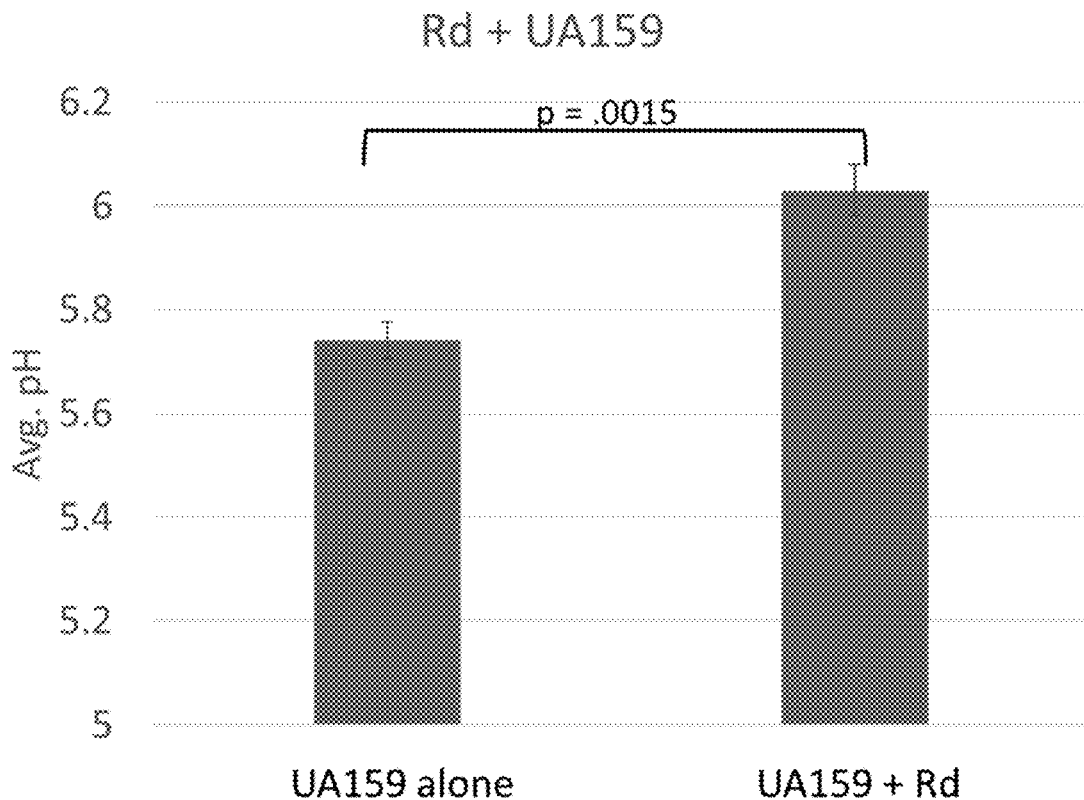
Figure 2D:
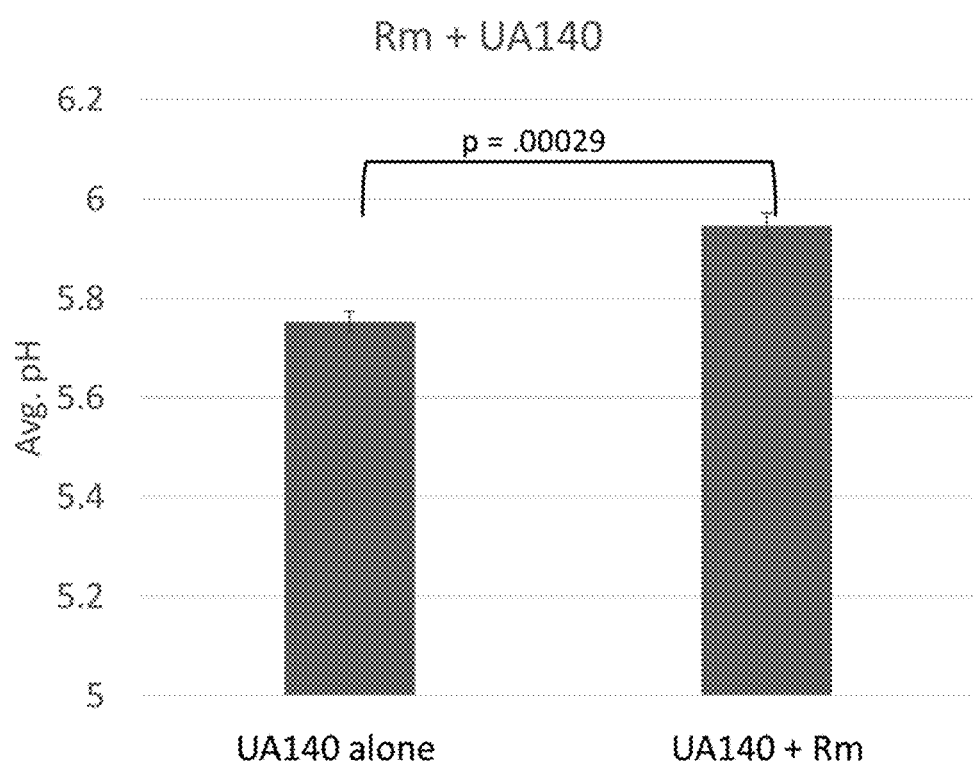
Figure 2E:
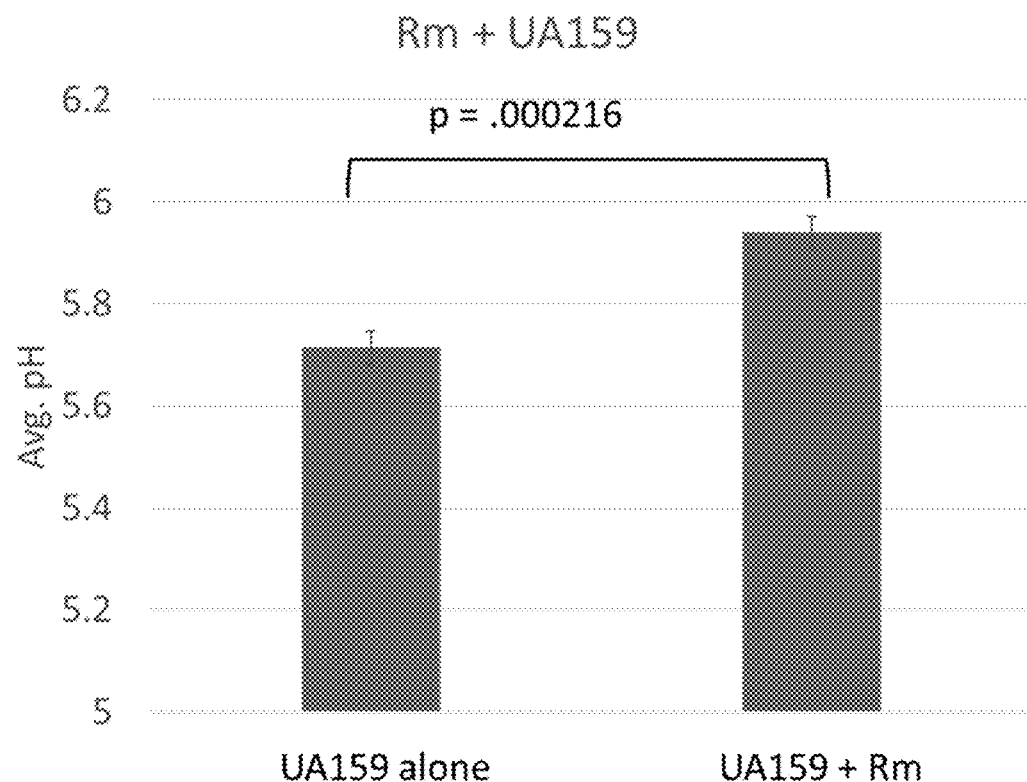
Figure 2F:
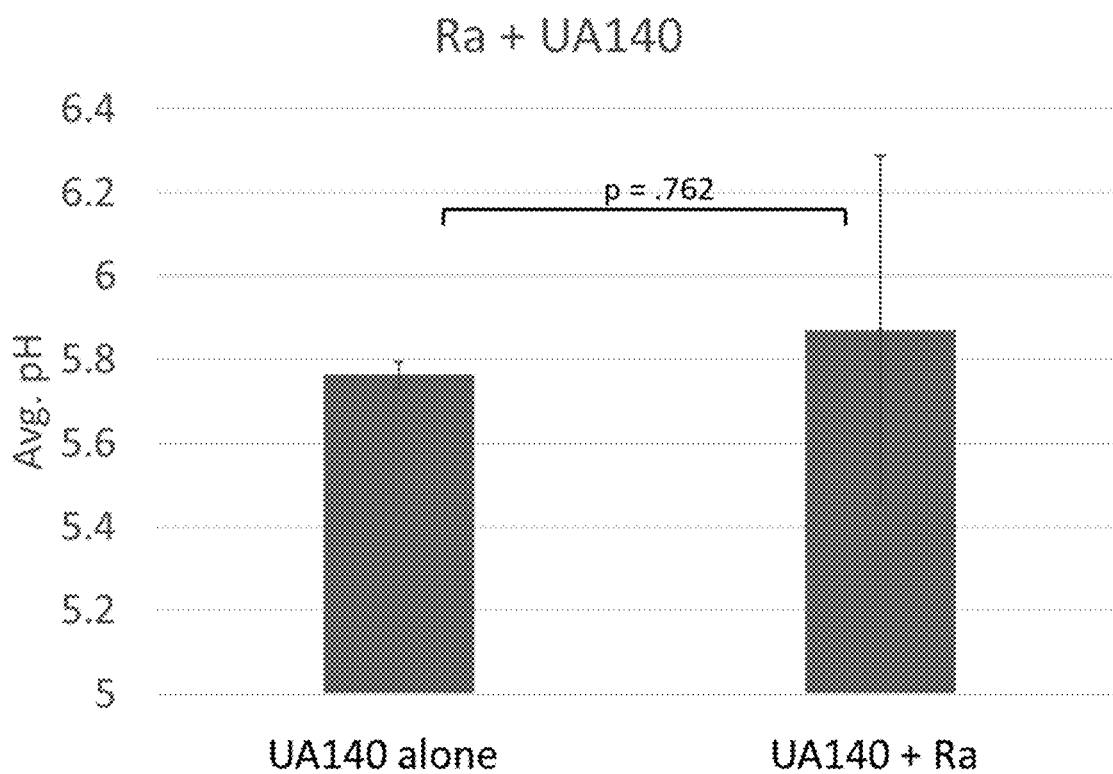
Figure 2G:
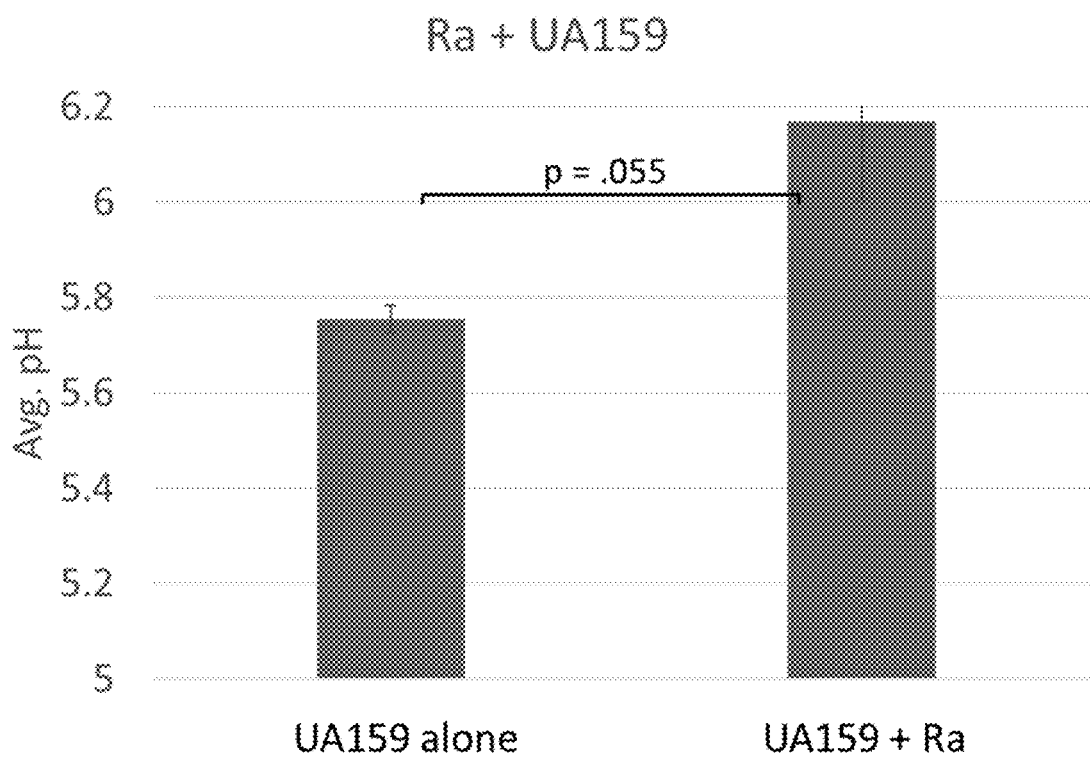

Protocol: The cells of Rd (*Rothia dentocariosa*) and Sm (*S. mutans*) (FIGS. 2B-2C), Rm (*Rothia mucilaginosa*) and Sm (FIGS. 2D-2E), or Ra (*Rothia aeria*) and Sm (FIGS. 2F-2G) were grown overnight at 37° C. in shaking aerobic or aerobic +5% CO2 conditions, respectively. The cell cultures had their optical density measured and were diluted to $OD_{600}$ 0.5 in fresh BHI liquid media. 20 µL of each culture were spotted onto a BHI agar plate with the pH indicator Phenol red, alone as well as adjacent to each other. After the 20 uL were spotted on the plate they were incubated overnight again in the aerobic +5% CO2 conditions The local pH of each spot was measured using a flat bottom pH probe at the center of the spot. See FIG. 2A. The experiments were performed in triplicate, the error bars represent the standard deviation, Student's T-test was used to determine statistical significance.

Results: Colonies of Sm had significantly higher pH when grown next to colonies of *Rothia* cells compared to Sm colonies grown alone (FIGS. 2B-2G).

Example 5: Soft Agar Setup

Figure 3A:
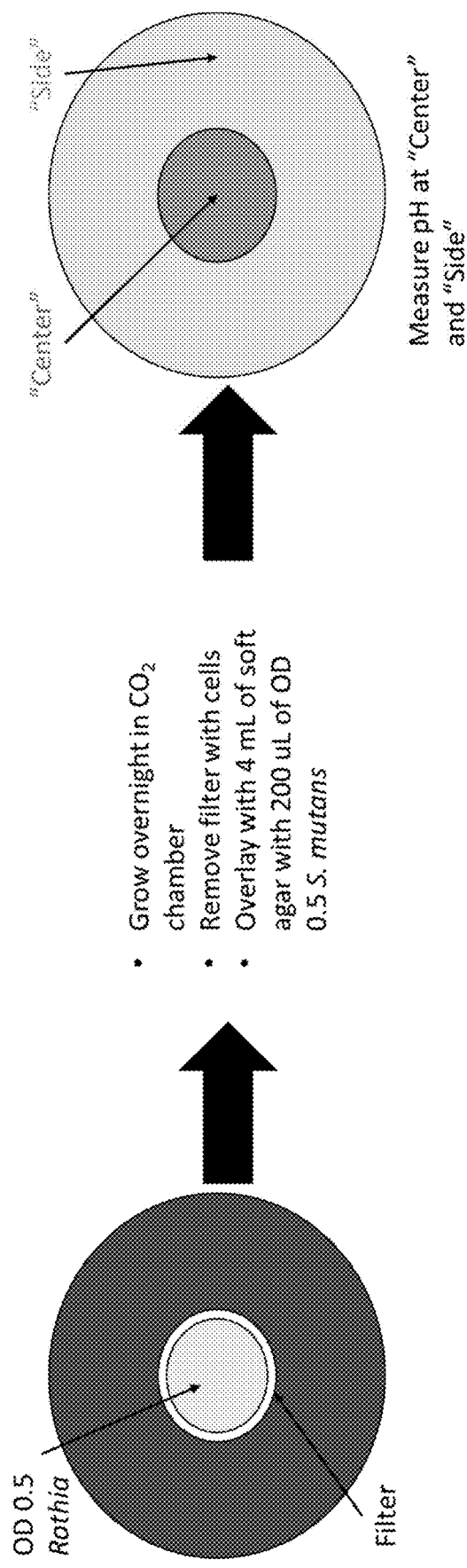
FIG. 3A shows a schematic diagram of the soft agar setup.

The soft agar setup is shown in FIG. 3A.

Goal: Separate the inhibitory bacterial species and Sm physically and their growth temporally. This controls for nutrition and competition as each species used has its own source of nutrition.

Protocol: Place a 0.22 μm filter on center of the BHI agar plate with phenol red and measure the $OD_{600}$ of overnight cultures of the different *Rothia* species or other candidate inhibitors. Dilute the bacterial cultures to $OD_{600}$ 0.5, spread them on filter and grow overnight in their respective growth conditions. This prevented bacteria from physically contacting the agar surface while allowing molecules <0.22 μm in size to pass through the filter and reside in the agar. After overnight growth, remove the filter bearing the bacterial cells and overlay the plate with 4 mL of BHI soft agar (0.5% agar) with phenol red containing 200 uL of $OD_{600}$ 0.5 Sm. Immerse the Sm cells in BHI soft agar (BHI media with 0.5% agar to solidify it, but allow for bacteria to survive and grow while immersed in it) and covering the surface of the plate with it allows us to separate Sm from the inhibitory bacteria both physically and temporally. When the soft agar solidifies, it was incubated overnight at 37° C. in aerobic +5% $CO_2$ conditions. The next day pH values were taken at the center of the plate and the side of the plate.

*Rothia* and Sm were temporally separated because the inhibitors were grown on a filter on the plate the day before the Sm overlay. They were physically separated because the cells were immersed in the semi-solid soft agar and thus did not touch the plate. They were also physically separated because the inhibitory cells were grown on top of a filter and when that filter was removed, it removed all the cells with it. The center measurement represents the pH when Sm was grown on the same location as the inhibitory bacteria while the side measurement represents the pH when Sm was grown in the absence of other bacteria.

Example 6: All Three *Rothia* Inhibited Acid Production in UA140 and UA159 without Physical or Temporal Contact Protocol: Place a 0.22 μm filter on center of the BHI agar plate with phenol red and measure the $OD_{600}$ of overnight cultures of the different *Rothia* species or other candidate inhibitors. Dilute the bacterial cultures to $OD_{600}$ 0.5, spread them on filter and grow overnight in their respective growth conditions. This prevented bacteria from physically contacting the agar surface. After overnight growth, remove the filter bearing the bacterial cells and overlay the plate with 4 mL of BHI soft agar (0.5% agar) with phenol sred containing 200 uL of $OD_{600}$ 0.5 Sm Immersing the Sm cells in BHI soft agar and covering the surface of the plate with it allowed to separate Sm from the inhibitory bacteria both physically and temporally. When the soft agar solidifies, it was incubated overnight at 37° C. in aerobic +5% $CO_2$ conditions. The next day pH values were taken at the center of the plate and the side of the plate. The experiments were performed in triplicate. The error bars represent the standard deviation and the statistical significance was determined using Studen't T-test.

Figure 3B:
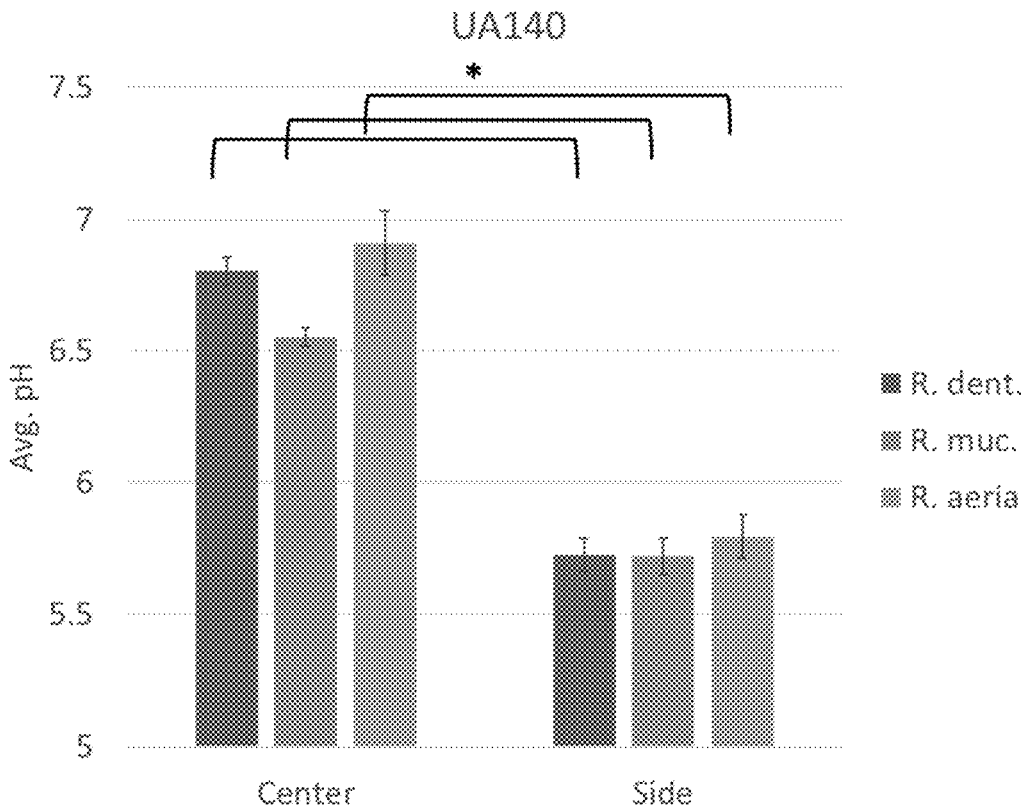
FIG. 3B shows that all three *Rothia* inhibited acid production in UA140 (*Streptococcus mutans* UA140) and UA159 (*Streptococcus mutans* UA159) without physical or temporal contact.
Figure 3C:
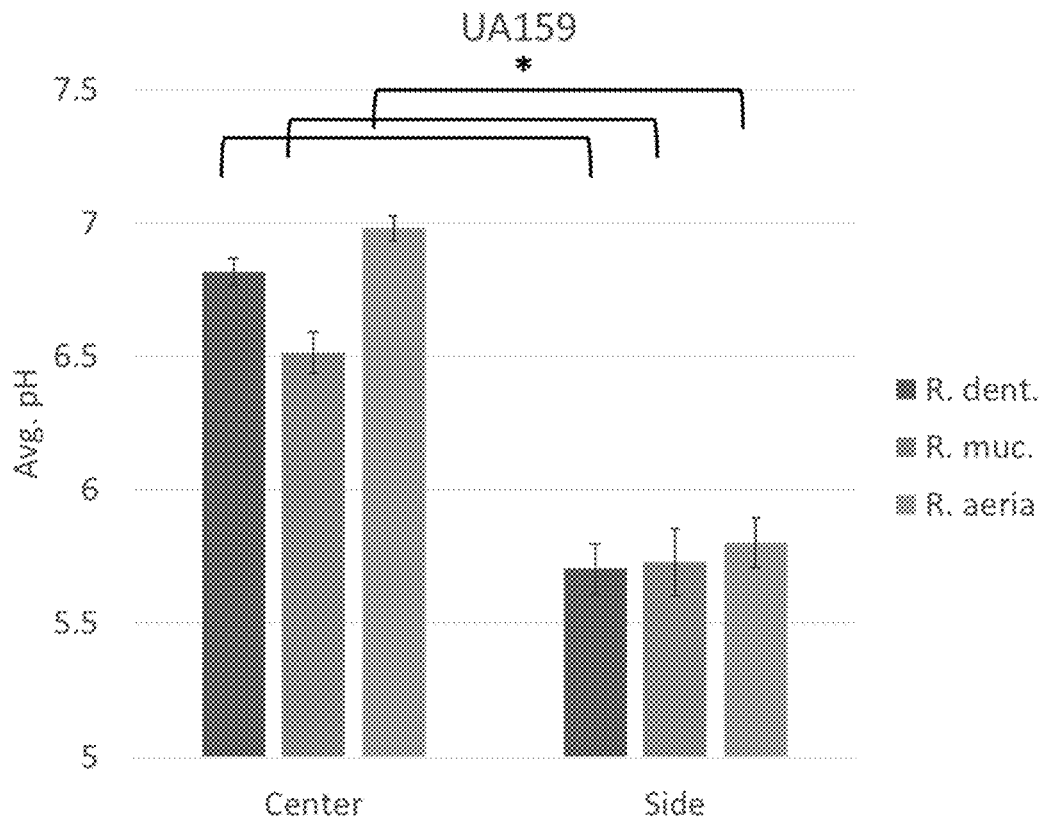
FIG. 3C shows that Rd (*Rothia dentocariosa*) inhibited acid production in non-Sm oral acid producers.

Results: The *Rothia* successfully inhibited the acid production of both Sm UA140 and UA159 in this way (FIGS. 3B and 3C).

Example 7: Rd can Inhibit Acid Production in Non-Sm Oral Acid Producers

Goal: This experiment shows if Rd can inhibit the acid production of other oral acid producing bacteria or if this is an interaction unique to Sm.

Protocol: Place a 0.22 μm filter on center of the BHI agar plate with phenol red and measure the $OD_{600}$ of overnight cultures of the different *Rothia* species or other candidate inhibitors. Dilute the bacterial cultures to $OD_{600}$ 0.5, spread them on filter and grow overnight in their respective growth conditions. This prevented bacteria from physically contacting the agar surface while allowing molecules <0.22 μm in size to pass through the filter and reside in the agar. After overnight growth, remove the filter bearing the bacterial cells and grow cells of Rd, *Streptococcus infantis, Streptococcus sanguinis* SK36, *Streptococcus sobrinus*, and *Lactobacillus fermentum* in BHI overnight. Rd and *L. fermentum* were grown in aerobic conditions at 37° C. *S. infantis, S. sanguinis* SK36, and *S. sobrinus* were grown in microaerobic (2% 02, 5% CO2, balanced with Nitrogen), conditions at 37° C. Place a 0.22 μm filter on center of the BHI agar plate with phenol red and measure the $OD_{600}$ of overnight cultures of the different *Rothia* species or non-Sm acid producing bacteria. When the soft agar solidifies, it was incubated overnight at 37° C. in aerobic +5% $CO_2$ conditions. The next day pH values were taken at the center of the plate and the side of the plate. The experiments were performed in triplicate. The error bars represent the standard deviation and the statistical significance was determined using Studen't T-test.

Figure 3D:
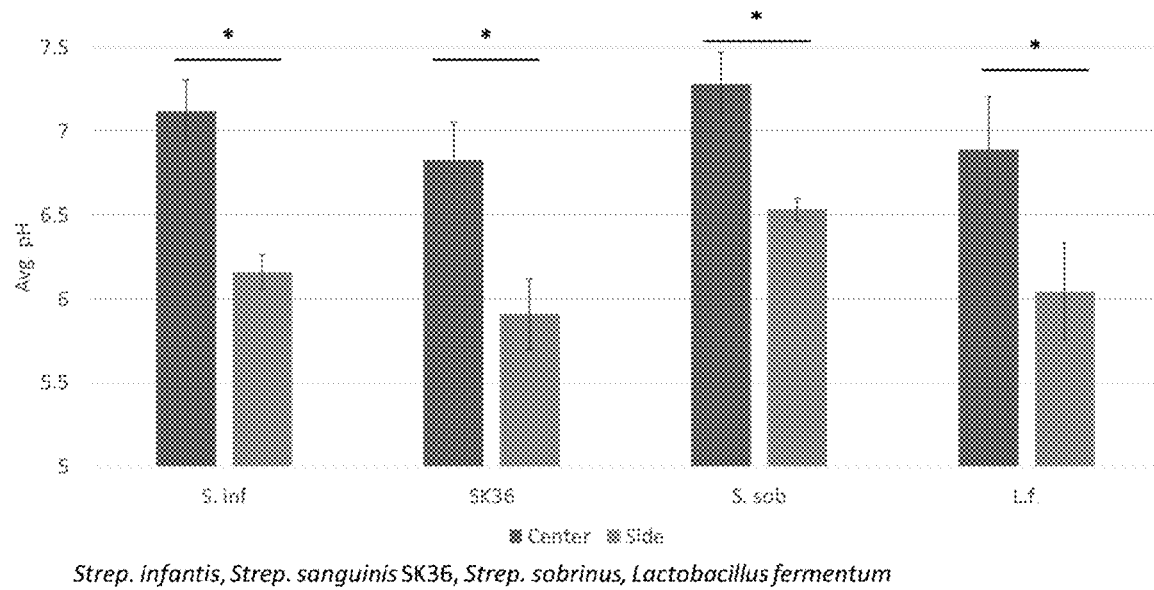
FIG. 3D shows that low starting pH (6.16) did not prevent *Rothia* from inhibiting Sm acid production.

Results: Rd inhibited the acid production of oral bacteria other than Sm (FIG. 3D). Similarly to its interaction with Sm, Rd inhibited the acid production of *Streptococcus infantis, Streptococcus sanguinis* SK36, *Streptococcus sobrinus*, and *Lactobacillus fermentum*. This data indicate that this is not a unique phenomenon between *Rothia* and Sm, though the mechanisms causing this inhibition of acid production may be different.

Example 8: Low Starting pH (6.16) Did not Prevent *Rothia* from Inhibiting Sm Acid Production Goal: Examine if lower pH has an impact on the ability for *Rothia* to inhibit the acid production of Sm.

Protocol: Place a 0.22 μm filter on center of the BHI agar plate with phenol red and measure the $OD_{600}$ of overnight cultures of the different *Rothia* species or other candidate inhibitors. Dilute the bacterial cultures to $OD_{600}$ 0.5, spread them on filter and grow overnight in their respective growth conditions. This prevented bacteria from physically contacting the agar surface while allowing molecules <0.22 μm in size to pass through the filter and reside in the agar. After overnight growth, remove the filter bearing the bacterial cells and overlay the plate with 4 mL of BHI soft agar (0.5% agar) with phenol red containing 200 uL of $OD_{600}$ 0.5 Sm. Immersing the Sm cells in BHI soft agar and covering the surface of the plate with it allowed to separate Sm from the inhibitory bacteria both physically and temporally. When the soft agar solidifies, it was incubated overnight at 37° C. in aerobic +5% $CO_2$ conditions. The next day pH values were taken at the center of the plate and the side of the plate. Plates with no *Rothia* grown on them, only the Sm immersed in soft agar, served as a control (Ctrl). The experiments were performed in triplicate. The error bars represent the standard deviation and the statistical significance was determined using Studen't T-test.

Figure 3E:
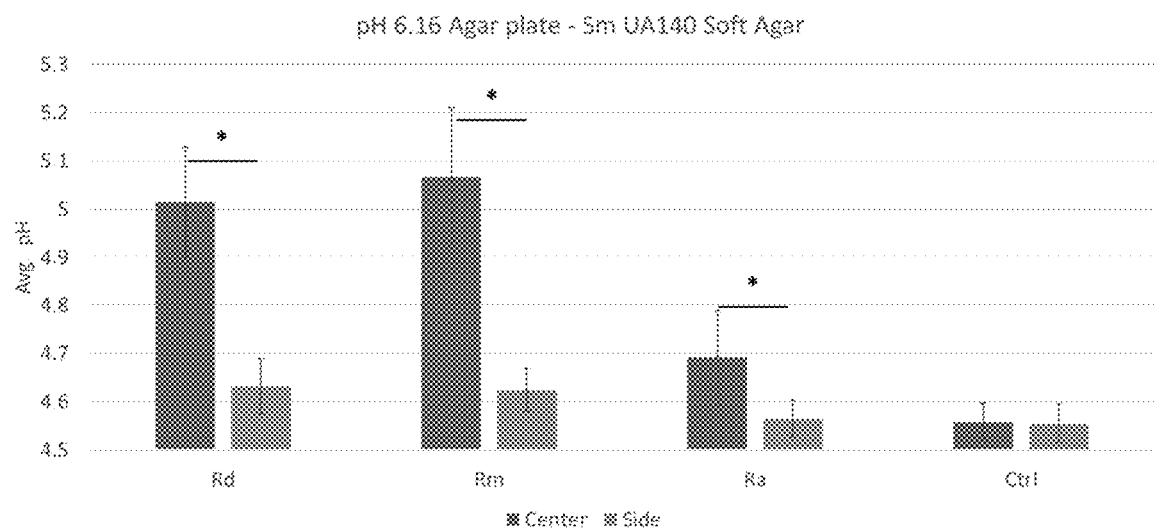
FIG. 3E shows that all three *Rothia* species significantly inhibited acid production of *S. mutans* even when the starting pH of the plate was lower than the normal plate pH (~7.4).

Results: All three *Rothia* species significantly inhibited acid production of *S. mutans* even when the starting pH of the plate was lower than the normal plate pH (~7.4) (FIG. 3E). This indicates that the local pH does not affect the ability of *Rothia* to inhibit acid production and therefore pH change.

Example 9: Staggered Inoculation Setup

The staggered inoculation setup is shown in FIG. 3E.

Goal: Determine if growth competition between the inhibitory bacteria and Sm played a role in the inhibition of acid production.

Protocol: The cells of *Rothia* were grown overnight at 37° C. in shaking aerobic conditions while Fn (*Fusobacterium nucleatum*) and Va (*Veillonella atypica*) were grown overnight at 37° C. in anaerobic conditions. Fn was grown in Columbia Broth and Va in BHI. The cell cultures had their optical density measured and were diluted to $OD_{600}$ 0.5 in fresh BHI media. 20 µL of each culture were spotted onto a BHI agar plate with Phenol red at two location. The spots were dried then put into their respective growth conditions overnight. The next day the process was repeated with Sm. The cells of Sm were grown overnight at 37° C. in aerobic +5% $CO_2$ conditions and diluted to $OD_{600}$ 0.5 in fresh BHI media the next day. 20 µL of the diluted Sm was spotted on the plate in two locations: one by itself and one adjacent to one of the spots of the inhibitor bacterial species. The plates were dried and incubated overnight at 37° C. in aerobic +5% $CO_2$ conditions and the pH of the Sm alone and the Sm co-culture colonies ("Co-Sm") were measured using a flat bottom pH probe.

Example 10: All Three Species Significantly Inhibited Acid Production in Sm UA140

Goal: Determine if growth competition between the inhibitory bacteria and Sm played a role in the inhibition of acid production.

Protocol: The cells of *Rothia* were grown overnight at 37° C. in shaking aerobic conditions. The cell cultures had their optical density measured and were diluted to $OD_{600}$ 0.5 in fresh BHI media. 20 µL of each culture were spotted onto a BHI agar plate with Phenol red at two location. The spots were dried then put into their respective growth conditions overnight. The next day the process was repeated with Sm. The cells of Sm were grown overnight at 37° C. in aerobic +5% $CO_2$ conditions and diluted to $OD_{600}$ 0.5 in fresh BHI media the next day. 20 µL of the diluted Sm was spotted on the plate in two locations: one by itself and one adjacent to one of the spots of the inhibitor bacterial species. The plates were dried and incubated overnight at 37° C. in aerobic +5% $CO_2$ conditions and the pH of the Sm alone and the Sm co-culture colonies ("Co-Sm") were measured using a flat bottom pH probe. The experiments were performed in triplicate. The error bars represent the standard deviation and the statistical significance was determined using Studen't T-test.

Figure 4A:
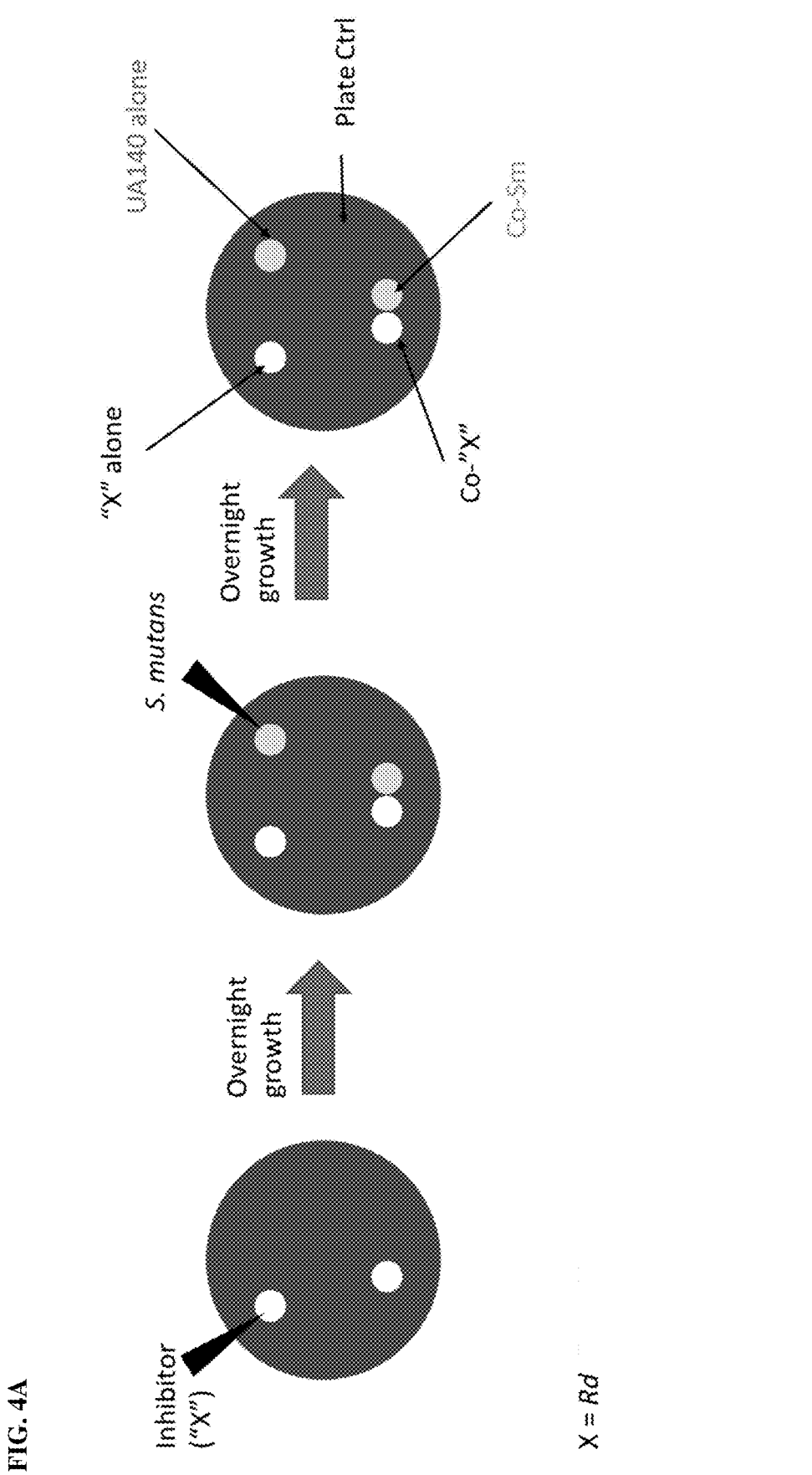
FIG. 4A shows a schematic diagram of the staggered inoculation setup.
Figure 4B:
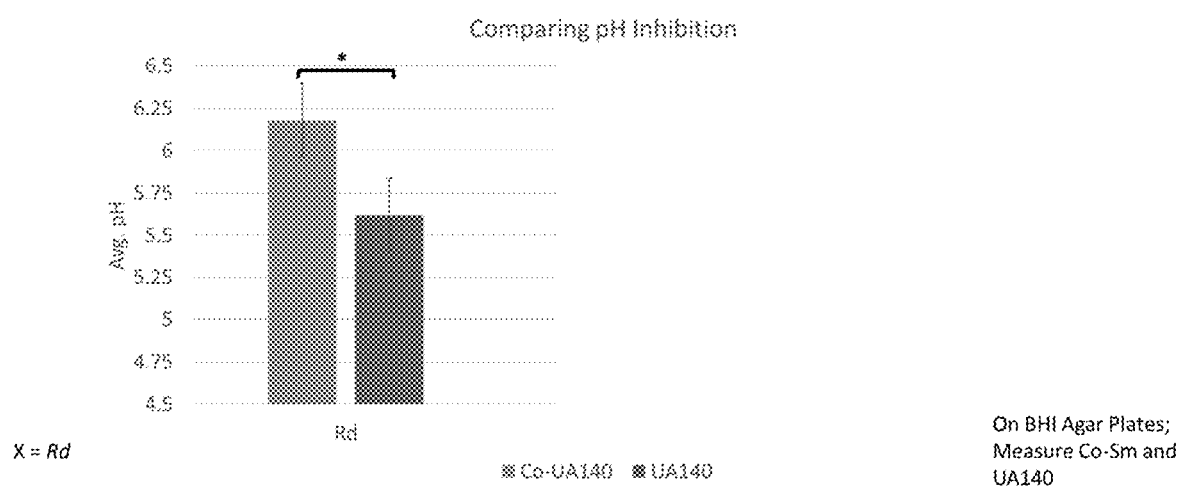
FIG. 4B shows that pre-grown Rd significantly inhibited acid production in Sm UA140.
Figure 4C:
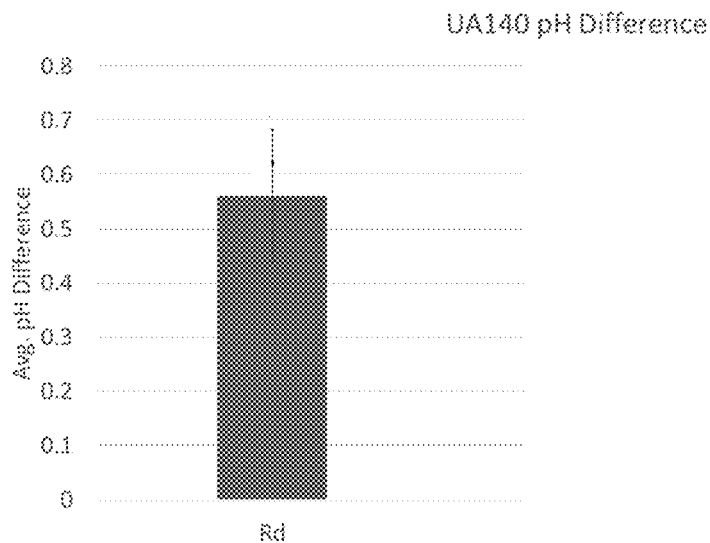
FIG. 4C shows the average increase in *S. mutans* pH induced by the presence of nearby pre-grown Rd colony.

Results: Rd species significantly inhibited acid production in Sm UA140 (FIG. 4B). This indicates that the acid inhibition is not due to growth competition between the inhibitory bacteria and Sm. This also indicates that Rd can inhibit the acid production of Sm, leading to an additive community effect on Sm.

Example 11: Rd Inhibited the Acid Production of Sm UA140

Goal: Examine the data from the staggered inoculation data to determine if there are significant differences in the ability of Rd to inhibit acid production.

Protocol: For each inhibitory bacteria test: Subtract the pH value of the Sm mono-culture from the Sm co-culture and determine average pH difference among all Center and Side pairs. The error bars represent the standard deviation and the statistical significance was determined using Student's T-test.

Results: These results show that Rd inhibited the acid production of Sm UA140.

Example 12: Other Observations

All three *Rothia* species can grow and remain viable in M9 Minimal Salts media, BHI media, and Oral *Rothia* species Selective Media (ORSM) (O. Tsuzukibashi et al. (2017) 134:21-26).

*S. mutans* UA140 out grew/out competed all three *Rothia* species when grown in co-culture (Sm+*Rothia*).

INCORPORATION BY REFERENCE

All publications and patent applications mentioned herein are hereby incorporated by reference in their entirety as if each individual publication or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of preventing dental caries in a subject comprising increasing the pH of the oral cavity of a subject in need thereof,
    wherein increasing the pH of the oral cavity of the subject comprises administering to the oral cavity of the subject a therapeutically effective amount of a bacterial composition comprising a bacterium of species *Rothia denticariosa*, a bacterium of species *Rothia aeria*, or a combination thereof.

2. The method of claim 1, wherein the bacterial composition prevents dental caries by inhibiting acid production by a cariogenic bacterium.

3. The method of claim 1, wherein the bacterial composition does not inhibit growth of a cariogenic bacterium.

4. The method of claim 1, wherein the cariogenic bacterium is a bacterium of species *Streptococcus mutans, Streptococcus infantis, Streptococcus sanguinis* SK36, or *Streptococcus sobrinus*.

5. The method of claim 4, wherein the bacterium of species *Streptococcus mutans* is a bacterium of strain ATCC UA140 or ATCC UA159.

6. The method of claim 1, wherein the cariogenic bacterium is a bacterium of genus *Lactobacillus*.

7. The method of claim 6, wherein the bacterium of genus *Lactobacillus* is a bacterium of species *Lactobacillus fermentum* and *Lactobacillus salivarius*.

8. The method of claim 1, wherein the subject is at risk of developing dental caries.

9. The method of claim 1, wherein at least 50% of the bacteria in the bacterial composition are bacteria of species *Rothia denticariosa, Rothia aeria*, or a combination thereof.

10. The method of claim 1, wherein at least 90% of the bacteria in the bacterial composition are bacteria of species *Rothia denticariosa, Rothia aeria*, or a combination thereof.

11. The method of claim 1, wherein substantially all of the bacteria in the bacterial composition are bacteria of species *Rothia denticariosa, Rothia aeria*, or a combination thereof.

12. The method of claim 1, wherein the bacterial composition comprises at least $1\times10^6$ colony forming units (CFUs) of bacteria of species *Rothia denticariosa, Rothia aeria*, or a combination thereof.

13. The method of claim 1, wherein the bacterial composition is administered orally.

\* \* \* \* \*

UNITED STATES PATENT AND TRADEMARK OFFICE
CERTIFICATE OF CORRECTION

| | | |
|---|---|---|
| PATENT NO. | : 11,872,255 B2 | |
| APPLICATION NO. | : 17/575160 | |
| DATED | : January 16, 2024 | |
| INVENTOR(S) | : Pooja Balani et al. | |

It is certified that error appears in the above-identified patent and that said Letters Patent is hereby corrected as shown below:

In the Specification

At Column 1, Lines 15-18, under the heading "STATEMENT OF RIGHTS":
Delete "numbers NIH-1-R01-DE020102" and
Insert -- number DE020102 --.

Signed and Sealed this
Seventh Day of May, 2024

Katherine Kelly Vidal
*Director of the United States Patent and Trademark Office*